United States Patent [19]
Hirleman, Jr. et al.

[11] Patent Number: 5,101,113
[45] Date of Patent: Mar. 31, 1992

[54] ENSEMBLE SCATTERING PARTICLE SIZING SYSTEM WITH AXIAL SPATIAL RESOLUTION

[75] Inventors: Edwin D. Hirleman, Jr., Mesa; Donald J. Holve, Danville, both of Ariz.

[73] Assignee: Arizona Board of Regents, Tempe, Ariz. ; a body corporate acting on behalf of Arizona State University

[21] Appl. No.: 352,358

[22] Filed: May 16, 1989

[51] Int. Cl.$^5$ .............................................. G01N 15/06
[52] U.S. Cl. .................................... 250/574; 356/336
[58] Field of Search ............... 250/574; 356/335, 336, 356/338, 342, 343

[56] References Cited

U.S. PATENT DOCUMENTS

| | | | |
|---|---|---|---|
| 3,809,478 | 5/1974 | Talbot | 356/71 |
| 4,027,973 | 6/1977 | Kaye | 356/73 |
| 4,140,395 | 2/1979 | Kreikebam | 356/336 |
| 4,827,144 | 5/1989 | Zaitsa et al. | 250/574 |
| 4,830,494 | 5/1989 | Ishikawa et al. | 356/336 |
| 4,839,528 | 6/1989 | Itoh | 250/574 |
| 4,850,707 | 7/1989 | Bowen et al. | 356/336 |

*Primary Examiner*—David C. Nelms
*Assistant Examiner*—John R. Lee
*Attorney, Agent, or Firm*—Richard R. Mybeck

[57] ABSTRACT

An ensemble scattering particle sizing system employing optical means and unique methodology which generates reliable data relative to particle concentration, size distribution and spatial distribution, including axial spatial distribution, for particles disposed in light transmitting medium gas with a given sample volume, means including a beam transmitter, a transform lens, an apertured image plane and a relay lens are strategically associated with a sample volume and detector means to produce the desired results.

20 Claims, 1 Drawing Sheet

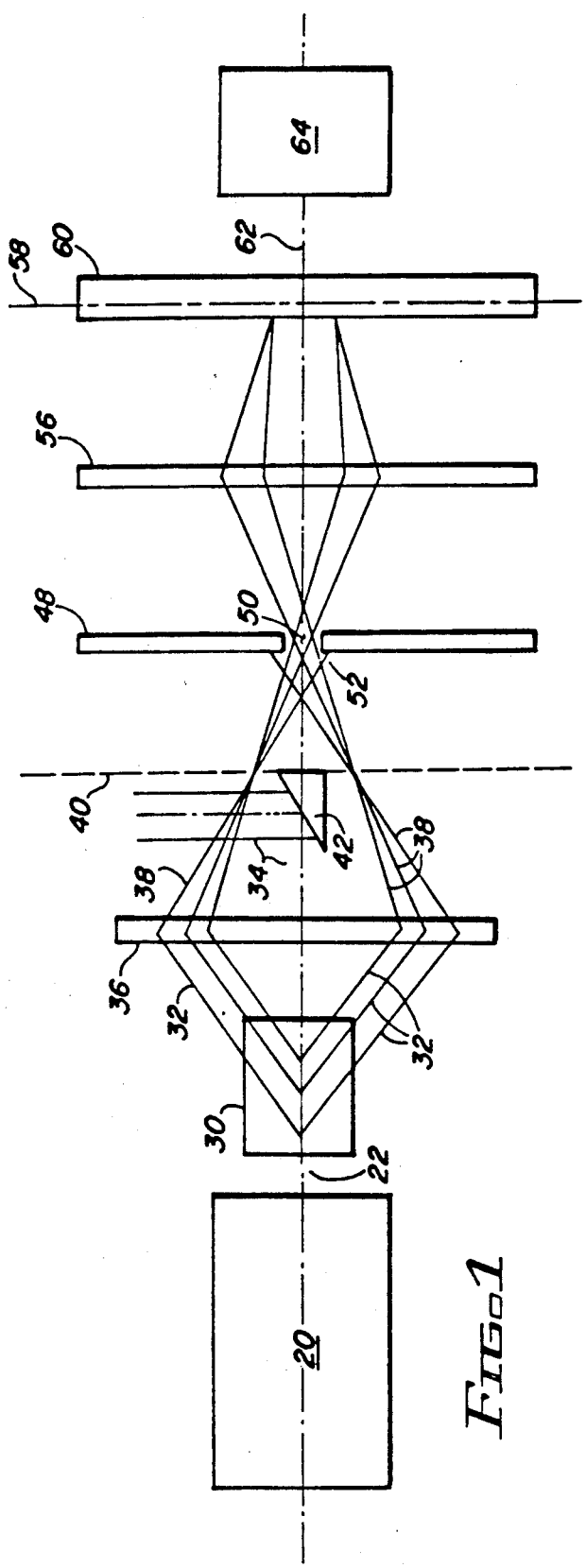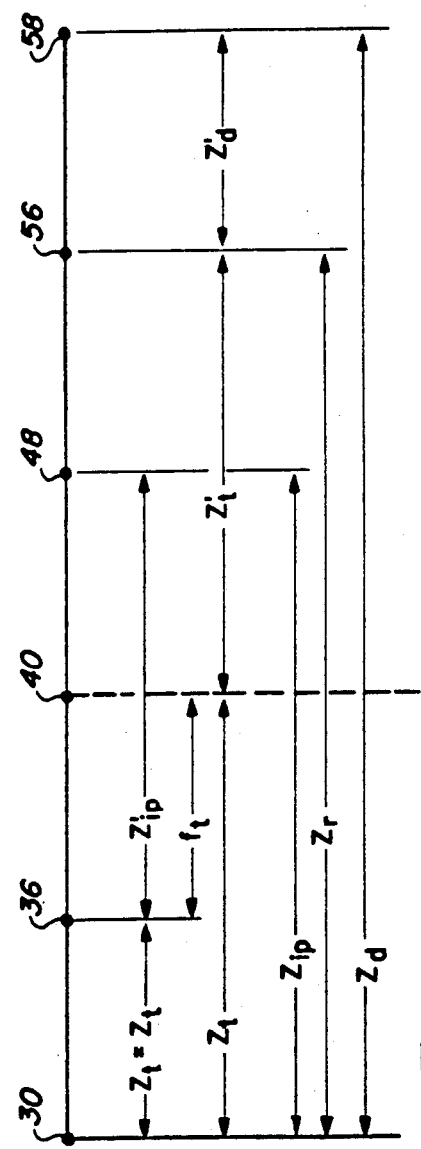

ENSEMBLE SCATTERING PARTICLE SIZING SYSTEM WITH AXIAL SPATIAL RESOLUTION

INTRODUCTION

The present invention relates to ensemble scattering particle sizing systems and more particularly to an optical system for obtaining axial spatial resolution in near-forward scattering (Fraunhofer diffraction) particle size measurements.

BACKGROUND OF THE INVENTION

The Fraunhofer diffraction particle sizing technique has become well accepted for characterizing both solid and liquid particles. This method is an ensemble technique which overages over the line of sight of the laser beam and this attribute is often considered a disadvantage in that the axial, that is, along the laser beam, spatial resolution is very poor.

The method disclosed here is based on analyzing the signature of light scattered in near-forward directions (i.e. in directions close to the progagation direction of the illumination beam) by ensembles of particles to determine various properties of the particle-population. Since scattering angles are by convention measured from the forward direction, the near-forward scattering directions are small angles. Also under certain common conditions, specifically particles large compared to the wavelength with refractive indices significantly different than the surrounding medium, the near-forward or small angle scattering properties are readily predicted or approximated by Fraunhofer diffraction theory. The relevant methods of interest are also referred to as "Fraunhofer diffraction technique".

The art of particle sizing and more particularly, the evolution of means for determining the concentration and size distribution of particles in a liquid or a gas using near-forward scattering patterns, which means is also capable of remotely measuring these properties with axial spatial resolution is a primary focus of the present invention.

Many commercial processes would benefit from on-line monitoring of liquid and gaseous suspensions. For example, the ability to characterize the size distribution of dispersed particles and droplets is of crucial importance in a number of practical systems. Some important applications include: liquid fuel droplets sprayed into air in combustion systems such as boilers and gas turbine combustors; solid particles dispersed in liquids as in coal-oil slurries; solid particles dispersed in combustion exhausts with respect to the health aspects of particulate pollutant emissions; and others. In many of these applications, optical (as opposed to batch) sampling techniques for particle sizing are advantageous and sometimes necessary. (The term particle will refer herein to both solid particulate matter and fluid droplets of diameters approximately 0.01 $\mu$m to 1 mm.)

A problem which is often encountered in measuring techniques is to determine the size distribution of physical entities, such as particles in a liquid or gas, gas bubbles in a liquid, or liquid droplets in liquids or gases. All of the various measurable entities will be herein referred to as "particles" and all references to "particle measurement" is intended to include the measurement of gas bubbles and droplets as well. This task is addressed and, to some extent alleviated by the systems described in a number of U.S. Patents, the disclosures of which are specifically incorporated herein by this reference thereto. The U.S. Patents referred to are: U.S. Pat. No. 3,469,921, Taylor; U.S. Pat. No. 3,636,367, Girard; U.S. Pat. No. 4,037,964, Wertheimer et al; U.S. Pat. No. 4,338,030, Loos; U.S. Pat. No. 4,251,733, Hirleman (I); U.S. Pat. No. 4,188,121, Hirleman (II); U.S. Pat. No. 3,835,315, Gravitt; U.S. Pat. No. 3,689,772, George et al; U.S. Pat. No. 3,988,612, Palmer; U.S. Pat. No. 4,360,799, Leighty; U.S. Pat. No. 4,740,677, Carreras et al; and U.S. Pat. No. 3,873,206, Wilcock.

Advanced optical systems for determining the particle parameter of size often use laser illumination of single particles and analysis of the scattered light characteristics to obtain information on the size and other physical parameters of a given particle. The sizes of many particles are measured and summed to determine the particle concentration and the overall particulate size distribution. The use of lasers is advantageous due to the greater light intensity available as compared to conventional light sources, thereby allowing measurement of smaller particles and enhancing the ability for in-situ or non-interfering measurements. Arrangements using white light scattered in only one solid angle require an extremely well defined and compact sampling volume through which a representative sample of the particulate flow must be passed.

In the system disclosed by Gravitt, supra, laser or other light is focused to intensely illuminate a small region in space. This region, called the sensitive volume or particle sampling zone, is located in the field of light collecting apparatus which discriminates between the light scattered at two small angles and the light traveling in the light beam propagation direction. Detector means are used simultaneously to detect and record signals representing the intensities of the scattered light detected at the different angles. A measure of one of the parameters, i.e. the particle size, of a particle passing through the sampling zone is determined by measuring the ratio of the signals representing the intensities of the scattered light detected at two angles. This measurement is, however, non-unique or ambiguous since particles of different sizes may pass through the sampling zone and since many particle sizes can generate the same ratio signal.

One problem with a laser system is the Gaussian intensity distribution in the beam, since single angle systems can not differentiate between a small particle passing through the high-intensity center of the beam and a larger particle passing through an off-center point of lower intensity. This problem can be eliminated by utilizing the ratio of light intensities scattered in two directions thereby cancelling the incident intensity effect as suggested by Gravitt.

Hirleman I discloses a technique for measuring particle size and velocity using two beams of electromagnetic radiation with symmetrical radial intensity distributions directed through space. A particle sampling volume is defined by those portions of the two beams within the field of view of one or more radiation sensitive detectors. The detectors respond to scattered radiation or fluorescence from particles passing through the beams in the sampling volume. The detector output for a single particle indicates two signal pulses corresponding to those times when the particle was in one of the beams. The speed of the particle in the plane perpendicular to the beams is determined from the transit time or width of the signal pulses, and the angle of the particle traverse in that plane determined from the time-of-flight between the signal pulses.

Hirleman II discloses an improved multiple ratio single particle counter in which intensities of scattered radiation are measured at more than two angles and the ratios of these intensities are derived. The derived ratios are then compared with calibration curves to determine an unambiguous measure of the particle parameter.

The family of methods which use the aggregate scattering properties of an ensemble or population of particles are herein termed "ensemble scattering" techniques.

The simplest example of an ensemble scattering method using near-forward small-angle scattering comprises a light transmitter creating a beam of light, a sample through which the beam of light is directed, and a plurality of discrete detectors disposed in a preselected angular relationship to the central axis of the light beam and to each other. The photodetectors are placed at a multiplicity of angles and collect light scattered in the various directions. Equivalently, a single detector might be translated (as in a goniometer) through various angles and the scattered light readings recorded. To obtain a particle-position-independent response from a conventional system as described above requires that the detectors be disposed very far away from the particles, where "far away" means would require distances many times greater than the extent of the illuminated portion of the particle field which is often impractical. However, the placement of a lens on axis in the scattered light field will effectively convert an angular scattered light distribution in the far-field to a radial distribution at the back focal plane of the receiving lens. This was done by Chin et al in 1955. (See: *Journal of Physical Chemistry*, vol. 59, 1955, p. 841.) It turns out that the E-field distribution of the scattering signature at the back focal plane of the lens is the Fourier transform of the E-field distribution, one focal-length in front of the lens. For this reason, the back focal plane is called the "Fourier transform plane" or the "transform plane". It also occurs that the scattering at the transform plane is essentially independent of the position of the scattering particle(s). For that reason detection of the scattering is often performed at the transform plane, and hence this plane is also often called the "detection plane". The particle measurement art then includes a scheme of segregating and detecting the scattered light irradiance at a multiplicity of positions in the detection plane. Chin et al, supra, traversed a small photodetector behind a small aperture across the detection plane to register the scattering signature.

In ensemble scattering particle sizing it is necessary to measure light scattering at a multiplicity of angles to infer particle size distribution. Generally in the optical system, the transform lens converts the far-field angular diffraction pattern into a spatial distribution of scattered light at the transform or detection plane. In the prior art, there were a number of concepts developed for sampling the scattering or diffraction pattern. In the earliest work, researchers translated a single detector with a pinhole aperture across the diffraction pattern to obtain measurements at roughly even increments of the scattering angle. A major shortcoming of this technique arose from the fact that the intensity in the diffraction pattern drops off rapidly from the near-forward (near on-axis) angles to larger off-axis angles. This results in a signal dynamic range which is often too large for a single detector in practical environments where noise is a problem. Similar difficulties are encountered when a solid state detector array is used having equal area detector elements.

A very general method to compress the dynamic range required of detectors is to utilize a detection strategy whereby the detector aperture(s) increase in area as the distance from the optical axis (diffraction pattern center) is increased. This approach provides the largest area in those regions of the diffraction pattern where the intensity is the lowest.

The ring detector comprises an array of concentric annular detectors on a single silicon wafer with areas which increase with radial distance from the detector center. This detector which had a series of wedge-shaped detector elements on the other half, was manufactured by Recognition Systems, Inc. (RSI).

Since the Fraunhofer diffraction pattern possesses circular symmetry, the rings and wedges sample the diffracted energy in polar coordinate form. That is, the rings sample the distance of the diffraction pattern portions from the axis, while the wedges sample the direction at which portions of the pattern are disposed. A suitable wedge-ring detector, having 32 rings and 32 wedges, is disclosed by George et al in U.S. Pat. No. 3,689,772.

Palmer, cited above, discloses a photodetector array system in which the array is comprised of a matrix of photodiode detectors, and may, for instance, be a 32 by 32 element device such as the Reticon model R32X32A.

Loos describes an arrangement for measuring the size distribution of particles suspended in a gas or in a liquid. In Loos, a spatial filter is placed in the exit plane of a dispersive element so that its transmittance is a function of position on the filter. Light transmitted by the filter is measured by a photodetector. The photodetector output is measured as different spatial filters are switched in place.

Wilcock and Wertheimer et al, supra, discuss a Fourier transform plane spatial filter in which a mask lies in the transform plane of the lens while in Taylor, supra, the size distribution of an aggregation is determined by the amount of light in a ring in the Fourier plane. Girard describes a Fourier transform optical analyzer which uses a mask shifted step by step relative to an optical object support.

While the above-cited references are instructive, the task of measuring particle size distribution in liquids and in gas, particularly in a manner which permits axial spatial resolutions to be obtained, remains an ongoing need. These methods are all line-of-sight methods in which all particles in the laser beam scatter light into the detector plane.

Some efforts have been made to overcome this deficiency by taking multiple independent measurements by passing the laser beam through various sections of the particle field. Abel inversions (for symmetric aerosols) or tomographic reconstruction methods are then used to obtain spatially resolved data. In addition to being a convoluted procedure, these later techniques still leave uncertainty to the credibility of the data obtained. Thus, a need still exists for the provision of a relatively quick and highly credible procedure for obtaining axial spatial resolution in Fraunhofer diffraction particle size measurements. It is toward the resolution of this need that the present invention is directed.

BRIEF SUMMARY OF THE INVENTION

The present invention presents a new and unique ensemble scattering particle sizing system which provides highly credible axial spatial definition. The invention adds a significant new capability to the conventional near-forward ensemble scattering method. Credible axial spatial resolution is obtained by the present invention which introduces a plurality of additional optical components, herein referred to as "image plane spatial filtering", which coact with a novel and unique modeling aspect. The results provided hereby have heretofore been unobtainable with previously available technology.

Specifically, the present invention is predicated upon a light scattering technique to measure the angular properties of light scattered from a large ensemble of particles. The method hereof has been conformed to provide axial spatial resolution from ensemble measurements. Spatial resolution of less than 20-30 mm for particles of less than 50 microns in size is obtainable.

The present invention includes a device for determining the particle concentration and size distribution and axial spatial resolution in a liquid or a gas using near-forward scattering patterns. It involves a light source, a sample volume, a transform lens to collect scattered light, an image plane aperture, a relay lens and detector means. The light source will be either pulsed or continuous. As will appear, the coaction of the image plane aperture and the relay lens provide spatial resolution. By inserting the image plane aperture and the relay lens, the detector means receives light from only a small segment of the laser beam rather than the entire line-of-sight illuminated by the beam.

Accordingly, it is a prime object of the present invention to provide an ensemble scattering system for determining particle concentration and size distributions with axial spatial resolution.

A still further object of the present invention is to provide a new and improved ensemble scattering particle sizing system which generates signals that are directly correlative to particle population properties referenced in three dimensions.

These and still further objects as shall hereinafter appear, are fulfilled by the present invention in a remarkably unexpected fashion as can be readily discerned from the following detailed description of a preferred embodiment thereof, especially when read in conjunction with the accompanying drawings in which like elements bear like indicia throughout the several views.

DESCRIPTION OF THE DRAWINGS

In the drawings:

FIG. 1 is a diagramatic showing of an ensemble scattering particle sizing system embodying the present invention; and FIG. 2 is a schematic showing of the axial dimensional relationship of the components of the system of FIG. 1.

DETAILED DESCRIPTION OF THE PREFERRED EMBODIMENT

The present invention is a device for determining the particle concentration and size distribution using near-forward scattering signatures and more particularly to a system which provides axial spatial resolution.

FIG. 1 is a schematic of the laser diffraction particle sizing system with axial spatial resolution in accordance with the present invention. The system of FIG. 1 can be used to determine the particle size distribution from near-forward scattering patterns, using: a light source, a transform lens, an image plane aperture, a relay lens, and a detector means.

In the system of FIG. 1, the collection of particles forming the sample volume 30 may, for example, be a population of fluid-suspended particles either contained within an enclosure or in a flowing stream. That sample is placed in a position such that a light beam 22 is directed at the particles as by the transmitter 20 which is shown in FIG. 1 directing a light beam 22 along the optical axis of the system. Particles which are in the sample volume and lie in the path of the light beam 22 cause a scattering or deflection of some portions 32 of the light beam. The scattered light is refocused by a focusing element which consists of the transform lens 36 through the first detection plane 40 into the image plane 48. That portion of the refocused light which passes through the image plane aperture 50 is focused by the relay lens 56 on detector 60. The detector 60 in turn produces on its output lines 62 signals which are read into the computer 64.

All of the hardware elements in the system hereof are commercially available and can be used to determine the particle concentration and size distribution at a remote location.

The transmitter section of the system comprises a light source which emits an illuminating beam which is passed through the sample volume. The light source may be a laser, a laser diode, or some other well-collimated incoherent source. The light beam 22 coming out of the transmitter must be of sufficiently low divergence (that is, sufficiently well collimated) so that significant energy is carried at angles where particle sizes of interest scatter substantial light. The collimation requirement may be obtained using a laser as the light source and passing that light through a spatial filter assembly mounted in the transmitter. Since large particles preferentially scatter light into small angles, it is the largest particle size of interest which will dictate the maximum divergence of the light beam 22. Further, the spectral band width of the light beam 22 must be a small fraction of the average wavelength. Incoherent light sources can be used to meet these requirements. The light beam 22 will preferably be 5-10 times larger than the largest particle size of those particles in the sample volume to ensure that the incident optical wavefronts are approximately planar across the particle. When a laser light source is employed, a beam expander may be necessary to create the preferred light beam diameter.

The light beam 22 is then directed to the sample volume containing the particles herein measured and a transform lens is selected. If the system is to be operated in the nominal 1:1 imaging condition, the working distance between the transform lens to the center of the sample volume will be two focal lengths ($2f_t$). The sample may contain particles, droplets, bubbles and the like which, for convenience, will be herein "particles".

The size of the image plane aperture is determined based on the desired length of the optical sample volume. A first approximation of the length of the optical sample volume for a given scattering angle can be calculated by:

$$L = m_t P / Q$$

where:
  L is the axial length of the optical sample volume;
  $m_t$ is the magnification employed at the transform lens;
  P is the radius of the image plane aperture;
  Q is the scattering angle;
  $m_t = Z_t/Z'_{ip}$; and
  $1/f_t = 1/Z_t + 1/Z'_{ip}$ wherein $Z_t$ is the object distance from scatter to receiver lens 36 and $Z'_{ip}$ is the image distance from receiver lens 36 to image plane aperture Next, the relay lens 56 is selected by focal length and positioned. Finally, the detection plane 58 is located for placement of detector means 60 as shown in FIG. 1. The position of the second detection plane 58 is related to the position of the relay lens by the equation:

$$1/f_r = 1/Z'_{tr} + 1/Z_{dr}$$

The scattering pattern taken to the detection plane is magnified by $m_r$ wherein:

$$m_r = Z_{dr}/Z_{tr}$$

Thus, light scattered at angle Q from the sample region will reach a radial position of the transform plane at $Z_t$ according to the equation:

$$r_t = fQ$$

When the ray at an angle Q passes through the image plane aperture, it will strike the second detection plane at a radial position ($r_d$) where:

$$r_d = m_r r_t = m_r R_t Q$$

Thus, the detector means, that is, the photodiode ring detector, the field detector behind the mask at the detection plane, or the translating aperture/detector at the detection plane provide the scattering signature as a function of angle. A beam stop is interposed in the system to eliminate unscattered light from the measurements.

A beam stop 42 may be placed at the transform plane, either as an opaque block or as an optical fiber to direct the light out of the optical light system to a transmitted light detector. The beam stop is centered in the detection plane.

The use of previously known mathematical inversion routines will provide the desired particle size distribution. A more detailed description of the theory underlying the effectiveness of the present invention appears in the paper published by Hirleman and Holve in the Proceedings of the 4th European Symposium on Paricle Characterization and presented at Nurnberg West Germany, April 19-21, 1989. That article is incorporated herein by this reference thereto.

To measure the particle population properties at a sequence of locations along the Z or optical axis using this invention, two methods may be used. First, the entire instrument can be relocated such that the center of the sample volume is also relocated.

The detector means implemented at the second detection plane may take various forms. Photodiode detector arrays with ring-shaped elements may be used. Each of the ring detectors would output a signal proportional to the amount of incident scattered energy. A central, on-axis detector element may be used to measure the amount of light which is not particle-deflected and travels through the optical system. The amount of light deflected by particles out of the light beam is the same as the difference between the total light transmitted undeflected when no particles are in the sample volume and that transmitted, undeflected light when particles are in the sample volume. This deficit ratio, called the "extinction", is used to calculate particle concentration. by either of two methods: (a) the ring detector signal distribution provides size information (using Beer's Law, the particle concentration is computed from the ring detector measurement of D32 and extinction measured at plane 40 or 58); (b) all ring detector signals are added to obtain the total scattered light signal. (The particle concentration is proportional to the ratio of scattered light to the transmitted light measured at 40. D32 is then computed using Beer's Law). The two methods are equivalent. The second method is advantageous for more dilute solutions and allows the costly ring detector to be eliminated when detailed size distribution information is not required. In another embodiment, an aperture is drilled in the center of the photodiode array detector and a separate detector element placed just behind (+Z) the second detection plane 58 to measure the light transmission.

Other detector means could comprise an array of transmission masks at the second detection plane followed by a field lens and field detector.

Another detector means would involve programmable apertures at the second detection plane. First, note that the element to be used in the second detection plane is a commercially-available spatial light modulator. Such use was described by Hirleman et al in "Faraday-effect Light Valve Arrays for Adaptive Optical Instruments", Laser Institute of America, 1987, the disclosure of which is incorporated herein by reference, and repeated in part below.

In Fraunhofer diffraction particle sizing annular ring detector elements are advantageous, and an annular detector can be configured by switching to transparent a set of pixels in a circular pattern. Note that the detector transmission masks which can be produced with this concept will approach a perfect ring. Note also that the ring detector can be configured about any instantaneous center, a feature which is crucial for the use of laser diffraction particle sizing applications in combustion environments where refractive index gradients cause the incident laser beam to be deflected causing catastrophic effects for fixed geometry ring detectors.

This light valve array design can be used to create a detector of virtually any geometry. Thus, an instrument with some level of intelligence could interrogate the scattering pattern, determine those scattering angles at which the particle size information is maximized, and then reconfigure the detector to sample more points (scattering angles) in those regions of most interest).

Several different means for producing the transmitting or absorbing pixels can be envisioned. A first prototype uses the Faraday effect which depends on the input light being linearly polarized. Liquid crystal light valves are another common technology which could be used to create a "light gate array" as required for this invention.

In a second method, the image plane aperture is varied and measurements are taken for the various aperture sizes while the other elements of the instrument are otherwise maintained in a static condition. Abel deconvolution techniques are then applied to the measurements to determine the variations of the particle properties in the axial direction.

It is of course apparent that the system hereof can be embodied in a probe or other portable tool with varying either the optics or the significance of the signals produced thereby and as such, are intended to be included within the scope of this invention.

While the invention has been described in its presently preferred embodiment, it is understood that such modifications, alterations and adaptations as may readily occur to the artisan confronted with this disclosure are included with the spirit of the present invention which is limited solely by of the scope of the claims appended hereto.

Accordingly, what is claimed is:

1. A method for measuring spatially resolved concentration and size distribution of particles comprising the steps of: passing a light beam through a sample of said particles to create particle-deflected and non-deflected light; directing said particle-deflected light through a transform lens to a first detection plane in which the angular distribution of scattered light is converted into a radial spatial distribution by the transform lens, said radial spatial displacement of scattered light being indicative of the size distribution of all said particles, said particle deflected light from said first detection plane being focused into an image plane, said image plane having an aperture defined therethrough for receiving a portion of said focused light and passing said portion into a relay lens to redirect said light onto a second detection plane in which said radial spatial displacement of scattered light is weighted by said aperture to create a signal correlative to the spatially resolved concentration and size distribution of said particles in a spatially-resolved region of said light beam.

2. A method according to claim 1 in which said sample particles are suspended in fluid.

3. A method according to claim 2 in which said fluid is liquid.

4. A method according to claim 1 in which said light beam is a laser beam.

5. A method according to claim 4 in which said laser is a diode laser.

6. A method according to claim 1 in which said particle-deflected light defines 4024 parallel paths.

7. A method according to claim 1 in which said spatial distribution includes axial distribution.

8. A method according to claim 1 in which said light beam is created by a pulsed light source.

9. A method according to claim 8 in which said pulsed light source is a laser.

10. A method according to claim 9 in which said laser is a diode laser.

11. A method according to claim 1 in which the diameter of said aperture in said image plane is variable.

12. A method according to claim 1 in which said non-deflected light is directed to a beam block disposed on the axial center line of said light beam.

13. A method according to claim 1 in which said relay lens includes meaning for varying the magnification and focal length thereof.

14. A method according to claim 1 in which said transform lens includes means for varying the magnification and focal length thereof.

15. A method according to claim 1 in which an optical fiber is disposed at said first detection plane in position to receive said undeflected light and transmit said light to a remote detector.

16. A particle sizing system for selectively determining concentration, size distribution and/or spatial distribution in liquids and gases of a particle sample volume using near-forward scattering techniques, said system comprising: illuminating means for lighting said particle sample volume and causing particle-deflected and non-deflected light beams to emanate therefrom; means for receiving said non-deflected light beams and diverting said beams; first detector means for receiving said diverted non-deflected light beams and converting said beams into an non-deflected beam signal; a transform lens to receive and focus said particle-deflected light beams emanating from said particle sample volume to convert the angular distribution of scattered light into a radial spatial displacement of light and create an image; image plane means receiving said image from said transform lens and having an aperture defined therein for receiving and passing a portion of said radial spatial displacement light therethrough; a relay lens for receiving said portion of said transformed light passing through said image plane aperture and redirecting said light and a second detector means including conversion means for receiving said redirected light from said relay lens and converting said light into a signal which, in conjunction said undeflected beam signal, is correlative to the spatially resolved concentration and size distribution of said particles in a spatially-resolved region of said light beam.

17. A particle sizing system according to claim 16 in which said illuminating means comprises an illuminating laser beam and a beam expander.

18. A particle sizing system according to claim 17 in which said beam expander receives and expands said illuminating laser beam and expands the transverse diameter of said illuminating beam until it is at least 5 to 10 times greater than the longest linear measurement of the largest particle in said sample volume.

19. A particle sizing system according to claim 16 in which said illuminating means comprises a diode laser.

20. A method according to claim 1 in which said method is repeated varying the position of one or more of the transform lens and the image plane aperture to produce signals correlative to the spatial distribution of particles.

* * * * *